US011720168B1

(12) United States Patent
Jadidian et al.

(10) Patent No.: US 11,720,168 B1
(45) Date of Patent: Aug. 8, 2023

(54) INFERRED BODY MOVEMENT USING WEARABLE RF ANTENNAS

(71) Applicant: Microsoft Technology Licensing, LLC, Redmond, WA (US)

(72) Inventors: Jouya Jadidian, Los Gatos, CA (US); Mohammad Mustafa Malik, Snoqualmie, WA (US)

(73) Assignee: Microsoft Technology Licensing, LLC, Redmond, WA (US)

( * ) Notice: Subject to any disclaimer, the term of this patent is extended or adjusted under 35 U.S.C. 154(b) by 0 days.

(21) Appl. No.: 17/804,078

(22) Filed: May 25, 2022

(51) Int. Cl.
*G06F 3/01* (2006.01)
*G02B 27/01* (2006.01)
*H01Q 1/27* (2006.01)

(52) U.S. Cl.
CPC ......... *G06F 3/012* (2013.01); *G02B 27/0172* (2013.01); *G02B 2027/0134* (2013.01); *G02B 2027/0178* (2013.01); *H01Q 1/273* (2013.01)

(58) Field of Classification Search
CPC .......... G02B 27/0172; G02B 2027/014; G02B 2027/0178; G02B 2027/0134; G06F 1/163; G06F 3/011; G06F 3/015; G06F 3/017; G06F 3/0482; G06F 3/0485; G06F 3/04892; G06F 2203/014; G06F 3/012; G06N 3/0445; G06N 5/04; G06N 3/08; H01Q 1/273
See application file for complete search history.

(56) References Cited

U.S. PATENT DOCUMENTS

| 5,012,206 A | 4/1991 | Tigges | |
| 10,564,717 B1 * | 2/2020 | Shahmohammadi | ... G06F 3/015 |
| 10,635,179 B2 | 4/2020 | Shahmohammadi | |
| 10,877,558 B1 | 12/2020 | Zhao | |
| 11,481,031 B1 * | 10/2022 | Anderson | ............... G06F 1/163 |
| 2009/0219039 A1 | 9/2009 | Fasshauer | |
| 2019/0028635 A1 | 1/2019 | Inami | |
| 2019/0212822 A1 | 7/2019 | Keller et al. | |

(Continued)

FOREIGN PATENT DOCUMENTS

EP          0998659 A1    5/2000

OTHER PUBLICATIONS

U.S. Appl. No. 17/804,075, filed May 25, 2022.

(Continued)

*Primary Examiner* — Nelson M Rosario
(74) *Attorney, Agent, or Firm* — Alleman Hall Creasman & Tuttle LLP

(57) ABSTRACT

A method for a wearable computing device is presented. The wearable computing device includes one or more radio frequency (RF) antennas that are driven to expose a first body part of a user to an E-field. The first body part of the user located within a threshold distance of the RF antennas when the wearable computing device is worn by the user. Movement of the first body part of the user is determined based on changes in electrical conditions at the RF antennas over time. Movement of a second body part of the user is inferred based on the determined movement of the first body part, the second body part being located outside of the threshold distance of the RF antenna. The first and second body parts are coupled via interconnective tissues. An indication of the inferred movement of the second body part is output.

20 Claims, 7 Drawing Sheets

(56) References Cited

U.S. PATENT DOCUMENTS

2020/0382717 A1   12/2020   Chiu et al.
2021/0385379 A1   12/2021   Smith et al.

OTHER PUBLICATIONS

Alanis, et al., "3D Gesture Recognition Through RF Sensing", In Technical Report MSR-TR-2014-81, Jun. 2014, 14 Pages.

"International Search Report and Written Opinion Issued in PCT Application No. PCT/US22/028879", dated Aug. 9, 2022, 14 Pages.

"International Search Report and Written Opinion Issued in PCT Application No. PCT/US23/011098", dated Mar. 31, 2023, 12 Pages.

"International Search Report and Written Opinion Issued in PCT Application No. PCT/US2022/049928", dated Mar. 27, 2023, 13 Pages.

* cited by examiner

INFERRED BODY MOVEMENT USING WEARABLE RF ANTENNAS

BACKGROUND

Wearable computing devices provide the opportunity to position a plurality of sensors on or near the body of the user. Data obtained via these sensors may be used to monitor the user's health, capture user activities for subsequent training or analysis, and/or to generate realistic avatars that move, talk, emote, etc. along with the user.

However, for aesthetics, wearability, and in order to be made socially acceptable, wearable computing devices are limited in the number and type of sensors they can include. Most individuals are not interested in wearing elaborate sets of cameras, microphones, and other sensing devices in public settings. The sensors must then be constrained to be part of something that would normally be worn—eyeglasses, earrings, watches, belts, etc. As such, some useful information may not be captured directly. Indirect evidence and assumptions may produce incorrect or inaccurate data that could dissuade a user from relying on the device in critical situations.

SUMMARY

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. Furthermore, the claimed subject matter is not limited to implementations that solve any or all disadvantages noted in any part of this disclosure.

A method for a wearable computing device is presented. The wearable computing device includes one or more radio frequency (RF) antennas that are driven to expose a first body part of a user to an E-field. The first body part of the user located within a threshold distance of the RF antennas when the wearable computing device is worn by the user. Movement of the first body part of the user is determined based on changes in electrical conditions at the RF antennas over time. Movement of a second body part of the user is inferred based on the determined movement of the first body part, the second body part being located outside of the threshold distance of the RF antenna. The first and second body parts are coupled via interconnective tissues. An indication of the inferred movement of the second body part is output.

DETAILED DESCRIPTION

Near field electromagnetic (EM) sensors, such as radio frequency antennas may be placed on the lenses and/or chassis of a low-profile, socially-acceptable head-mounted display device or other "smart" eyeglasses to detect movement of facial features. Such sensors typically have a low signal to noise (SNR) ratio. As long as there are strong (e.g., higher SNR) signals from other sensors that may be combined with the EM sensors, the collective signals may be collected and combined to generate accurate readings.

Some facial movements are not able to be specifically captured, as there are no other sensors positioned or configured to target lower parts of the face (e.g., eyeglass-mounted sensors are spaced apart from lower parts of the face). As such, there are some specific facial expressions and mouth movements that are challenging to capture using frame-mounted antennas only, particularly for some head geometries, and/or if the user has selected a particular nose pad configuration. Jaw movements, cheek movements, and lip movements occur distally from the HMD device. Additional sensor information is thus needed to accurately capture these movements.

In some examples, additional sensor information is provided by microphones and eye-tracking cameras, allowing the HMD device to infer the position of the user's jaw, mouth, and facial features. Just based on audio signals captured by microphones, a reasonable rendering of the face, including lips and mouth movement can be generated based on audio signals that are presumed to be derived from speech of the user. However, some mouth movements are not accompanied by corresponding audible sounds (e.g., yawning, chewing gum), and thus that movement can be missed. A user listening to someone else speak may make numerous quiet facial expressions, indicating surprise, boredom, attentiveness, etc., which can carry a lot of information that is not otherwise conveyed.

In using this facial movement for avatar generation and rendering, a user's avatar may thus reflect more what is audibly happening in the user's environment, than what the user is actually doing. The avatar may be rendered to show a neutral facial expression when the user is not speaking, which may be off-putting to a second user that is observing the avatar for visual feedback.

Figure 1:
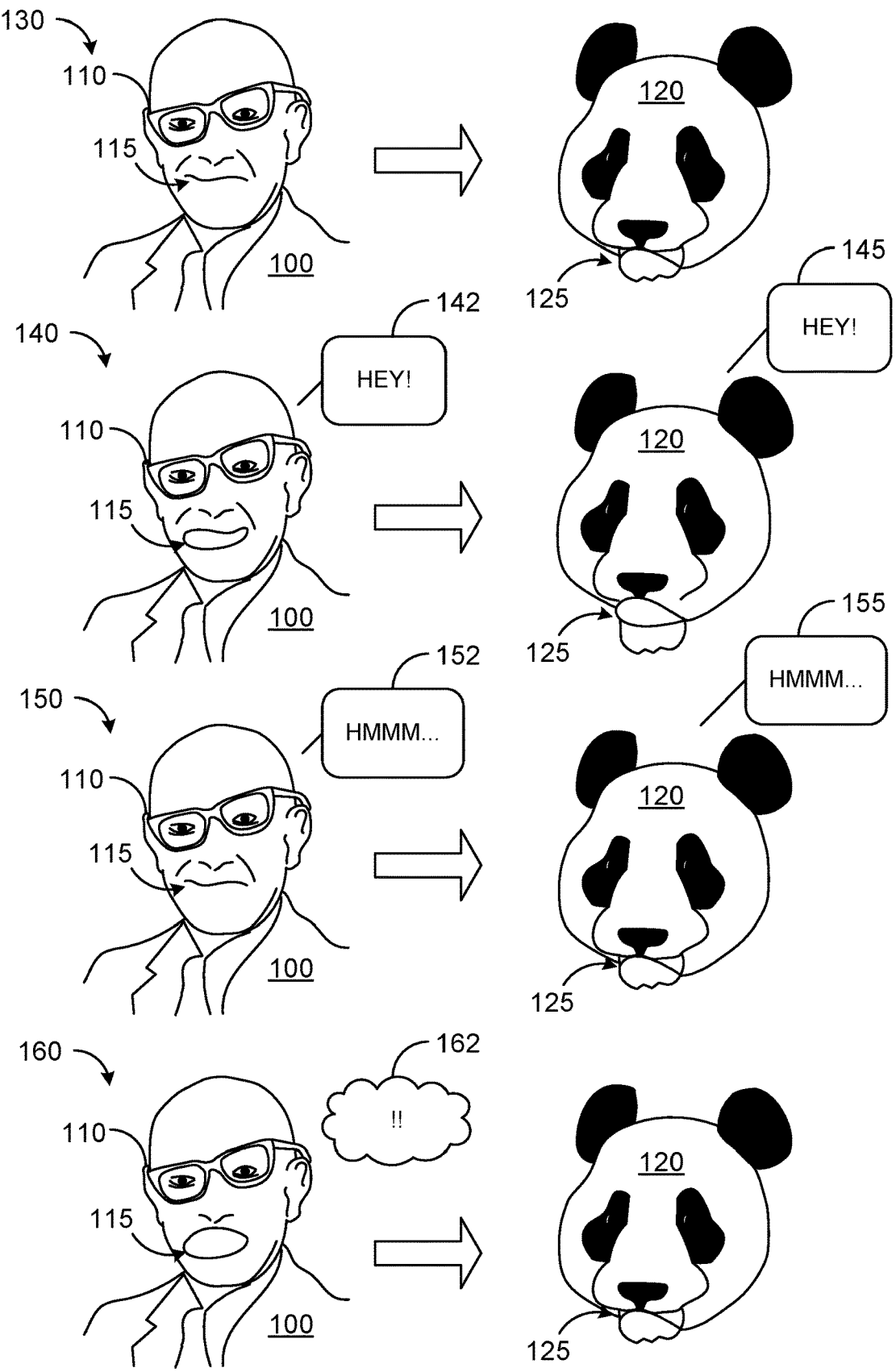
FIG. 1 illustrates a user wearing a head-mounted display (HMD) device and an avatar rendered based on signals captured by the HMD device.

FIG. 1 As an example, FIG. 1 shows a user 100 wearing an HMD device 110. HMD device 110 is configured to track movement of user 100, infer a position of the user's mouth 115, and provide this information for rendering of an avatar 120 featuring a corresponding mouth 125. At 130, user's mouth 115 is closed, as is corresponding mouth 125.

At 140, user 100 begins talking, as indicated at 142. User's mouth 115 opens, and corresponding mouth 125 is rendered to be open based on the speech patterns of user 100, conveyed as speech 145. At 150, user 100 continues verbalizing, as indicated at 152. User's mouth 115 closes, and corresponding mouth 125 is rendered to be closed based on the speech patterns of user 100, conveyed as speech 155.

At 160, user 100 opens user's mouth 115 in surprise, though no audible sounds are produced, as shown at 162. However, without an accompanying audio cue, avatar 120 is rendered so that corresponding mouth 125 is closed.

Audio based representations present other challenges due to audio bleed. For example, microphones may capture someone else talking, or ambient noise, such as typing, and assign this noise as speech of the user. Such background noise may be ascribed to speech patterns of the user, causing odd, garbled facial expressions to be rendered in an attempt to mimic sounds that the user is not actually making. Even with multiple microphones trained to perform noise cancellation, noises get through and can trigger changes in avatar appearance, even if the noise is not transmitted to other users. Practically, more than three microphones is prohibitive for space/cost/power constraints in an HMD device. Indeed, robust microphone beam forming may need 8 or more microphones.

More direct solutions, such as positioning a camera and microphone in from on the user' mouth are both awkward for the user and generally not considered socially acceptable. By using RF face tracking, the sensors are confined within a familiar form factor, which translates to how the device is perceived.

In general, wearable sensors are trained on body parts that are proximal to them. For the jaw, there is a significant spacing apart from the HMD device, and is not situated in a direct line to any existing sensors within this format. Herein, examples, are provided wherein the movement of the jawbone is inferred by measuring activity that occurs at the temple using RF antennas positioned in the temple piece of the HMD device. The two regions of the face are physically coupled by muscle, skin, tendon, and bones and thus movement of one necessarily impacts the other in an observable way. This concerted movement may be recorded and compared to previously recorded jaw movements to perform a classification. The RF antenna provides valuable diversity for verifying a large set of expressions by accessing jaw muscle group from the HMD device. In addition, the principle of RF antenna monitoring of one body part to infer movement of another body part may be extended to other wearable computing devices, such as wrist-worn computing devices.

Figure 2:
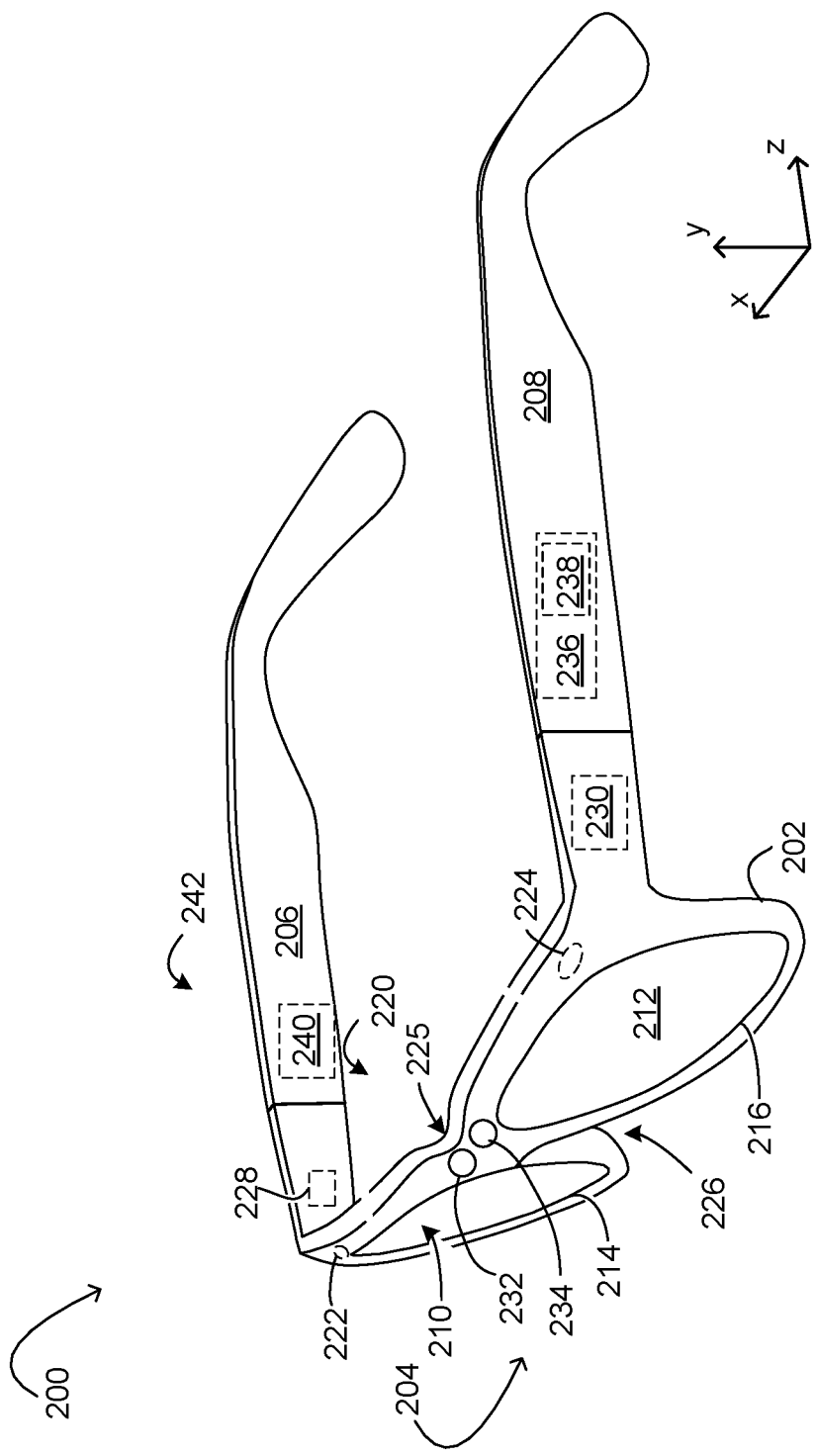
FIG. 2 shows one example of an HMD device.

FIG. 2 shows one example of an HMD device 200. The HMD device 200 includes a frame 202, a display system 204, and temple pieces 206 and 208. Display system 204 includes a first display 210 and a second display 212 supported by frame 202. Each of first display 210 and second display 212 include optical components configured to deliver a projected image to a respective eye of a user. HMD device 200 may be an example of HMD device 110.

Display system 204 of HMD device 200 includes a first display module 214 for generating and displaying a first image via first display 210 and a second display module 216 for generating and displaying a second image via the second display 212, where the first image and the second image combine to form a stereo image. In other examples, a single display module generates and displays first images and second images via first display 210 and second display 212, respectively. Each display module may comprise any suitable display technology, such as a scanned beam projector, a microLED (light emitting diode) panel, a microOLED (organic light emitting diode) panel, or an LCoS (liquid crystal on silicon) panel, as examples. Further, various optics, such as waveguides, one or more lenses, prisms, and/or other optical elements may be used to deliver displayed images to a user's eyes.

HMD device 200 further includes an eye-tracking system 220, comprising at least a first eye-tracking camera 222 and a second eye-tracking camera 224. Data from the eye-tracking system 220 may be used to detect user inputs and to help render displayed images in various examples.

Eye-tracking system 220 may further include a light source 225. Light emitted by light source 225 may reflect off of a user's eye and be detected by first eye-tracking camera 222 and a second eye-tracking camera 224. For example, reflections may be detected as bright spots on a surface of the user's eye. A location of the reflection relative to the user's eye may thus indicate a direction of the user's gaze.

In some examples, the light source and the camera of the eye-tracking system are both located on frame 202 HMD device 200. In some examples, small (e.g., 50 μm) light emitting diodes (LEDs) may be attached to the first display 210 and the second display 212. In other examples, a planar waveguide may be incorporated into the displays or adjacent layers to linearly guide eye-tracking light to one or more desired output location(s).

In this example, first eye-tracking camera 222 and second eye-tracking camera 224 are located at a right edge and a left edge of frame 202, respectively, and are configured to detect eye-tracking light reflected by the user's right eye and left eye, respectively. In other examples, left and right cameras can be located at other locations on frame 202, such as at the nose bridge portion 226 of frame 202. In some examples as described below, the eye-tracking light comprises infrared light and first eye-tracking camera 222 and second eye-tracking camera 224 comprise infrared cameras.

The position of the user's eye(s) may be determined by eye-tracking system 220 and/or gesture recognition machine 228. For example, eye-tracking system 220 may receive image data from first eye-tracking camera 222 and second eye-tracking camera 224, and may evaluate that data using one or more neural networks or other machine-learning devices. As an example, eye-tracking system 220 may determine the position of the user's eye based on the center point of the user's eye, the center point of the user's pupil, and/or gesture recognition machine 228 may estimate the location of the eye based on the location of the head-joint of the virtual skeleton.

HMD device 200 further includes an on-board computing system in the form of a controller 230 configured to render the computerized display imagery via first display module 214 and second display module 216. Controller 230 is configured to send appropriate control signals to first display module 214 to form a right-eye image of a stereoscopic pair of images. Likewise, Controller 230 is configured to send appropriate control signals to second display module 216 to form a left-eye image of the stereoscopic pair of images. Controller 230 may include a logic subsystem and a storage subsystem, as discussed in more detail below with respect to FIG. 5. Operation of HMD device 200 additionally or alternatively may be controlled by one or more remote computing device(s) (e.g., in communication with HMD device 200 via a local area network and/or wide area network).

HMD device 200 may further include various other components, for example an outward facing two-dimensional image camera 232 (e.g. a visible light camera and/or infrared camera), an outward facing depth imaging device 234, and a sensor suite 236. Sensor suite 236 may include one or more IMUs 238 which may include one or more accelerometers, gyroscopes, and/or magnetometers. IMUs 238 may be configured to generate positional information for HMD device 200 that allows for determining a 6OF position of the device in an environment. HMD device 200 may further include a plurality of components that are not shown, including but not limited to speakers, microphones, temperature sensors, touch sensors, biometric sensors, other image sensors, energy-storage components (e.g. battery), a communication facility, a GPS receiver, etc.

HMD device 200 may further include a face tracking system 240 and one or more RF face tracking arrays 242. RF face tracking array 242 may include a plurality of RF channels, each including on or more RF antennas. RF antennas may be placed at any suitable location on HMD device 200, including on frame 202, frame 202, temple pieces 206 and 208, first display 210 and second display 212. A ground reference may be established on the device chassis, such as on an earpiece of temple pieces 206 or 208. As will be described in more detail below, any or all of the plurality of RF antennas may be driven to influence electrical conditions in the vicinity of a human user. This may be done by driving the plurality of RF antennas to emit electromagnetic radiation having any suitable wavelength, amplitude, and/or other suitable characteristics.

Figure 3:
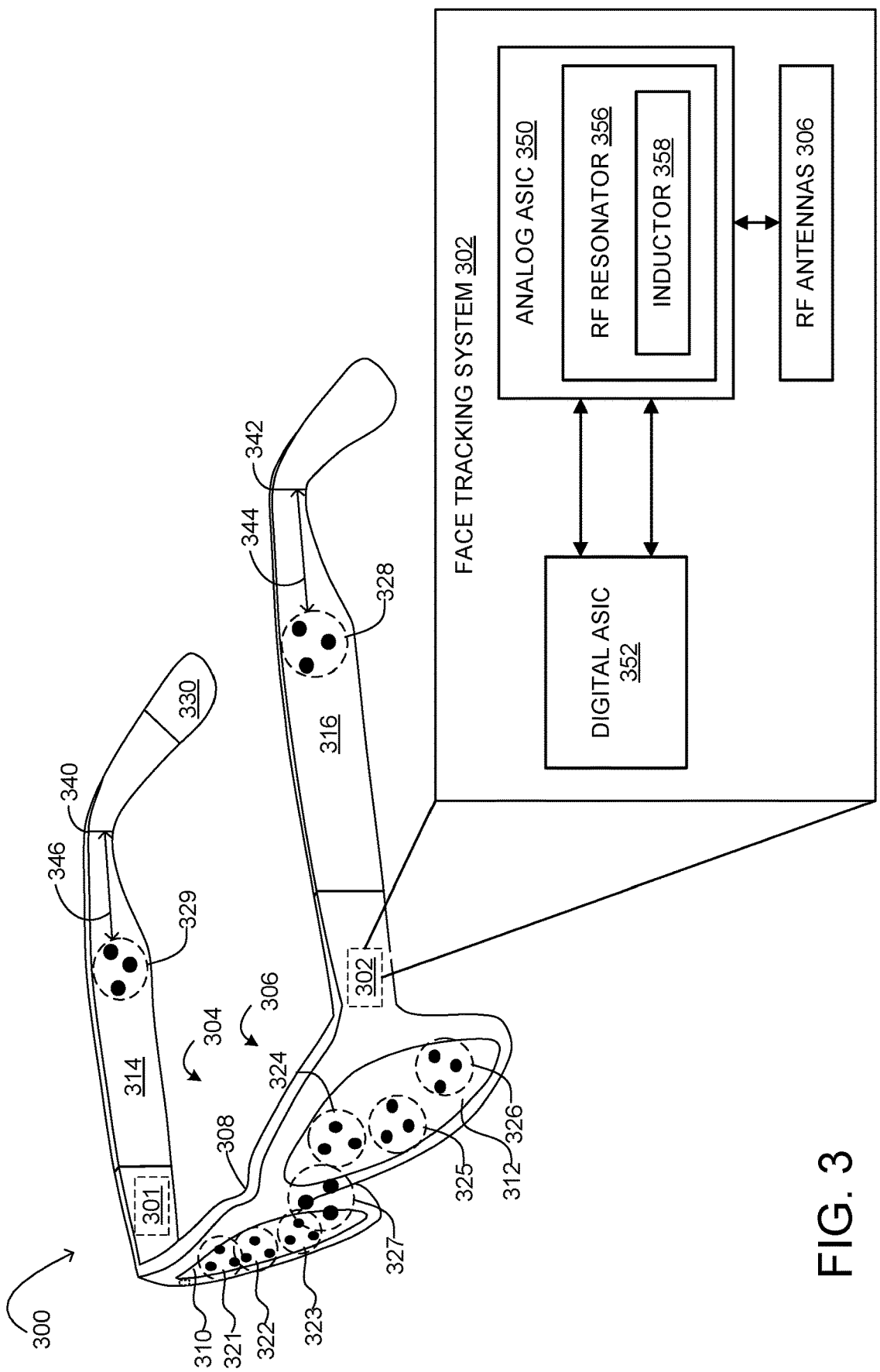
FIG. 3 shows an example of an HMD device including an RF face tracking system.

A more detailed example of a face tracking machine is shown in FIG. 3. HMD device 300 is shown to comprise controller 301, face tracking system 302 and RF face tracking array 304. HMD device 300 may be an example of HMD devices 110 and 200. Controller 301 may be an example of controller 230. Face tracking system 302 may be an example of face tracking system 240, and RF face tracking array 304 may be an example of RF face tracking array 242. HMD device 300 is shown in simplified form, but may include some or all of the components and functions described with regard to HMD device 200, as well as additional components and functions that are not described herein.

RF face tracking array 304 includes a plurality of RF antennas 306, represented by black circles disposed along frame 308, display 310 and 312, and temple pieces 314 and 316 of HMD device 300. It will be understood that this is done for the sake of illustration only—in practical examples, a computing device may include and/or interface with any suitable number of RF antennas. The plurality of RF antennas may each have any suitable positions relative to one another, the computing device, and the human user. For example, rather than integrated within a housing of the computing device as is shown in FIG. 3, the plurality of RF antennas may be physically separate from the computing device that classifies the human movement. For example, the RF antennas may be integrated into a wearable accessory that communicates with a separate computing device. Furthermore, the RF antennas may have any suitable appearance, and may or may not be visible to the human user and/or an outside observer.

In this example, RF antennas 306 are grouped into nine example RF channels (321, 322, 323, 324, 325, 326, 327, 328, and 329), illustrated by dashed lines around groups of 3 antennas. However, more or fewer antennas may be included in an RF channel, and the channels need not be comprised of equal numbers of antennae. More (e.g., 16) or fewer (e.g., 4) RF channels may be included. Antenna signals may be determined relative to ground 330—e.g., the device chassis. Ground 330 is shown at the end of temple piece 314, but any suitable position along the HMD device may be used.

RF signals received via display, outer frame, and nose bridge channels may be processed to look for presence and movement of cheeks, eyebrows, forehead, and nose. RF signals received via channels positioned on the temple piece (e.g., 328, 329), for example, may be used to look for the user's temporal regions. Each channel may aggregate two or more antennas, though in some examples, a channel may comprise only a single antenna. Groups of RF channels may be electrically coupled to a common relay, allowing for multiple channels to be activated or deactivated together. As more antennas and/or channels are made to be active, the more sensitive the face tracking machine can be, both in terms of detecting relatively small movements, as well as detecting movements over an increased distance.

Antennas positioned on or within displays 310 and 312 may be configured as relatively transparent wires. High transmission antenna types suitable for use on displays 310 and 312 include nanoweb, (a sub-micron, super conductive metal mesh), ITO, silver flakes, and nanowires. Antennas may be affixed to a substrate, or directly to the display materials, and may be sandwiched within a display or provide on the surface of a display.

Each individual RF antenna 306 may in some cases expose a different part of the human user's body surface to an E-field. For example, one or more RF antennas (e.g., 321-326) may generate an E-field in the vicinity of the user's eyes, while one or more other RF antennas (e.g., 327) may generate an E-field in the vicinity of the nose, and so on to achieve a desired coverage of the user's face. This may enable HMD device 300 to detect movements of the user's face, and classify such movements as predefined movements that serve as inputs to the computing device—e.g., different facial expressions.

For example, as human skin is conductive, proximity of the conductive human skin in a near-field region relative to the plurality of RF antennas may disturb an E-field generated by driving the plurality of RF antennas with drive signals, thereby influencing characteristics of the circuitry at one or more of the plurality of RF antennas. In particular, movement of conductive skin near an RF antenna (e.g., caused by movement of muscles under the skin) may affect the impedance at the RF antenna in a measurable way. This change in electrical conditions at the RF antenna may be useable to derive information relating to the user's movement. For example, a change in the distance between the conductive human skin and the RF antenna may result in a change in the electrical conditions at the antenna—e.g., detectable as a change in voltage. The user's movement may then be classified as one or more predefined human movements (e.g., recognizable gestures or facial expressions) by aggregating and interpreting data collected by the plurality of RF antennas.

In this manner, detected changes in electrical conditions at the plurality of RF antennas from one time frame to another may be used to evaluate movements of the human user between the two time frames. In particular, movement of the human user may change characteristics of a circuit that the user is also part of. As one example, the system may comprise an oscillator having a resonant frequency that is sensitive to changes in parasitic capacitance. In other words, the change in frequency of the oscillator may be caused by a change in capacitive loading at the user's body surface, and this may be affected by movements of the user.

The plurality of RF antennas may continue to expose the surface of the face of the human user to the E-field over a sequence of time frames. For example, the user's eyebrow may have lowered relative to the user's eye and either display 310 or 312. This movement of the human user (e.g., movements of muscles in the user's face) may influence electrical conditions at one or more of the plurality of RF antennas, as discussed above.

As described further herein, RF channels 328 and 329 may be driven to expose a temporal region of the user's face to an E-field. In some examples, only one of temple pieces 314 and 326 may include an RF channel. In such examples, counter-weights may be positioned as needed in the opposite temple piece that may correspond to regions of the circuit board and battery, so that frame tilting does not occur when glasses sit on face. The antennas may sit on the inner surface of the temple piece, rather than on the outer surface, so it can be close to the tissue that it's going to be interfacing with. Further, the outer surface of the temple piece may include other support electronics, such as wireless antennas, other communications antennas, and battery leads.

As will be described, to accurately gauge movement at the temporal regions, and thus to infer movement of the user's jaw and/or other connected facial regions, RF channels 328 and 329 may be positioned close the user's ear when HMD device 300 is worn, but not on the ear itself. Temple pieces 314 and 316 may be configured to sit on the ears of the user at points of contact 340 and 342, respectively. Channels 328 and 329 may thus be positioned at threshold distances 344 and 346 from points of contact 340 and 342, respectively, so that the pivoting of HMD device 300 at the ears during facial expression does not significantly decrease the SNR ratio of RF channels 328 and 329.

Face tracking system 302 may include electronic componentry that may be useable to implement and control a plurality of RF antennas, as described herein. For example, each RF antenna 306 may be communicatively coupled with an application-specific integrated circuit (ASIC) 350. As one non-limiting example, ASIC 350 may be an analog ASIC implemented via a BCD (bipolar-CMOS (complementary metal oxide semiconductor)-DMOS (double diffused metal oxide semiconductor)) process. BCD technology is beneficially more accessible in larger process nodes, while supporting relatively higher voltages associated with a higher Q-factor.

The analog ASIC may be communicatively coupled with a digital ASIC 352, which may use a relatively smaller process for digital blocks, while the analog ASIC is relatively larger to accommodate analog pins for a plurality of RF sensing channels. For example, the digital ASIC may use a CMOS process, while the analog ASIC uses a BCD process. The logical elements may use any suitable combination of hardware to drive and scan one or more RF antennas. For example, RF antennas 306 may be communicatively coupled with an RF resonator 356 and an inductor 358. These elements in combination may be useable to generate drive signals that, when supplied to RF antennas, cause the RF antennas to generate an E-field. It will be understood that the RF resonator and inductor may each take any suitable form, and that the specific arrangement of components depicted in FIG. 3 is non-limiting. For instance, in some examples, multiple RF resonators and/or inductors may be used to drive the plurality of RF antennas, even though only one RF resonator and inductor is shown in FIG. 3.

Face tracking system 302 may scan each of the plurality of RF antennas 306 to individually determine ground-relative changes in electrical conditions for each of the plurality of RF antennas relative to a previous time frame. For example, a change in electrical conditions detected at a particular RF antenna of the plurality of RF antennas may be caused by a change in a distance between the particular RF antenna and the human user while the body surface of the human user is exposed to the E-field.

The changes in electrical conditions may be expressed as measured changes in voltage ($\Delta V$) relative to a previous time frame, and/or as a change in current, amplitude, and/or signal phase. The framerate at which the plurality of RF antennas are scanned to determine ground-relative changes in electrical conditions may be independent from a framerate at which virtual imagery is displayed, and/or framerates at which any other computer operations are performed by the computing device. In this example, the changes in electrical conditions are ground-relative changes in electrical conditions, which include detected changes in voltage at each of the plurality of RF antennas relative to electrical ground 330 of HMD device 300. In other examples, however, the electrical conditions at each RF antenna may be compared to any suitable common reference.

As the changes in electrical conditions for each of the plurality of RF antennas are compared to a common reference (e.g., changes in voltage relative to the computing device ground), the plurality of RF antennas may each be driven to generate the E-field using drive signals having a same voltage and phase. In other examples, however, drive signals having different voltage and/or phase may be applied to two or more of the plurality of RF antennas in determining ground-relative changes in electrical conditions.

The specific frequencies used to drive the RF antennas, and the electrical characteristics of the larger circuit as a whole, may be tuned to achieve a desired level of sensitivity and power draw. Specifically, an RF antenna exposing conductive human skin positioned within a near field region relative to the RF antenna to an E-field may cause capacitive loading of the human skin. This may result in flow of complex or real current between the RF antenna and human user depending on the specific circuit design, the frequency of the drive signal, and the proximity of the human skin.

The computing device may determine a plurality of ground-relative changes in electrical conditions, and a plurality of antenna-relative changes in electrical conditions, for any or all of a plurality of RF antennas exposing the body surface of the user to an E-field. The computing device may then derive a plurality of orthogonal parameters from the ground-relative changes in electrical conditions and the antenna-relative changes in electrical conditions. The movement performed by the human user may then be classified as a particular predefined movement.

For example, the computing device may maintain a set of predefined movements, where each predefined movement is associated with a set of predefined orthogonal parameter values known to be consistent with that predefined movement. Thus, upon determining that a particular set of orthogonal parameters match a predefined set of parameters with at least a threshold similarity, then the detected human movement may be classified as the corresponding predefined movement.

For example, the observed set of orthogonal parameters may be used as values for a multi-dimensional feature vector, which may then be compared to similar vectors corresponding to each of the predefined movements via a suitable vector comparison process—e.g., by calculating a Euclidean distance. As another example, the detected parameters may be classified as predefined parameters based at least in part on suitable machine learning (ML) and/or artificial intelligence (AI) techniques. For example, the HMD device may include a machine learning trained-classifier configured to accept a set of orthogonal parameters as an input, and based on the parameters, classify the detected RF antenna output as one of a plurality of predefined movements. The machine learning-trained classifier may be trained in any suitable way and using any suitable training data—e.g., via a suitable combination of supervised and/or unsupervised learning.

Figure 4A:
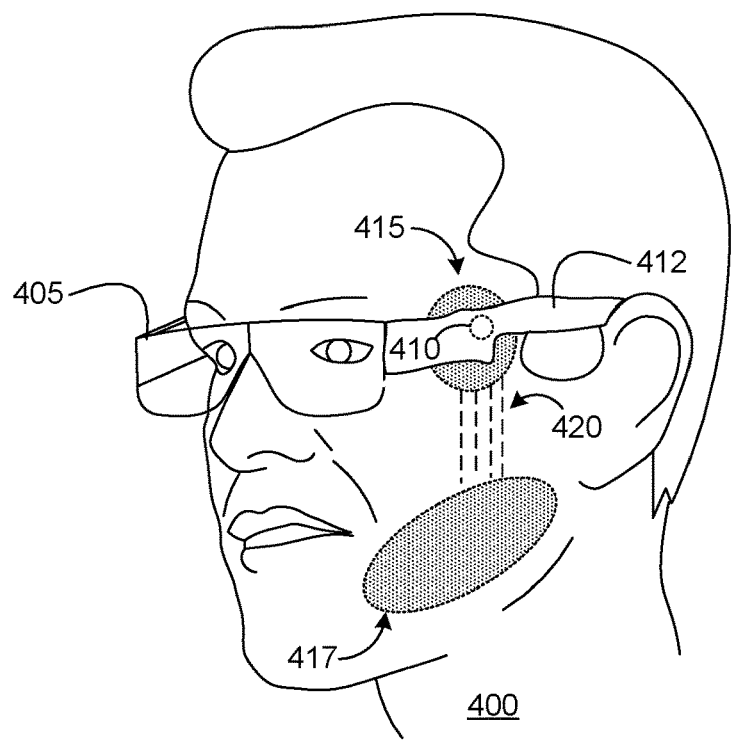
FIG. 4A shows an example of a user wearing an HMD device configured to infer facial movements using an RF face tracking system.

FIG. 4A illustrates a user 400 wearing an HMD device 405 including a RF antenna 410 positioned on an inner surface of a temple piece 412 of HMD device 405. HMD device 405 may be an example of HMD devices 200 and 300. As illustrated, RF antenna 410 is positioned a threshold distance from the ear of user 400 when HMD device 405 is worn.

While there is a significant population distribution with regards to head sizes and shapes, cheeks and noses, particularly across different ethnicities, the jaw muscle group, temporal muscles, and maxilla-facial regions are fairly consistent. As such, three to four temple piece lengths are sufficient to properly size 90% or more of the adult population temporal RF antennas, thus providing accurate coverage of jawbone movement. In some examples, the temple pieces of the HMD device may include adjustable sizing and/or adjustable RF angle of incidence to fine tune placement of RF antenna 410 for an individual. In some examples, various shapes of temple pieces may be available (e.g., straight, bowed away from the head). This may allow both for comfort and for performance of the face tracking system, and to allow the user to comfortably position the displays at a prescribed distance from their eyes.

RF antenna 410 may be driven to expose temporal region 415 to an E-field. Movement of temporal region 415 may be determined based on changed in electrical conditions at RF antenna 410. As the user's lower jaw region 417 moves, the interconnecting muscles and tendons 420 enact a force on temporal region 415, causing recognizable movements. With RF antenna 410 positioned close to the surface of the skin at temporal region 415, movement of facial tissues towards or away from the HMD device can be detected with a uniform response.

Figure 4B:
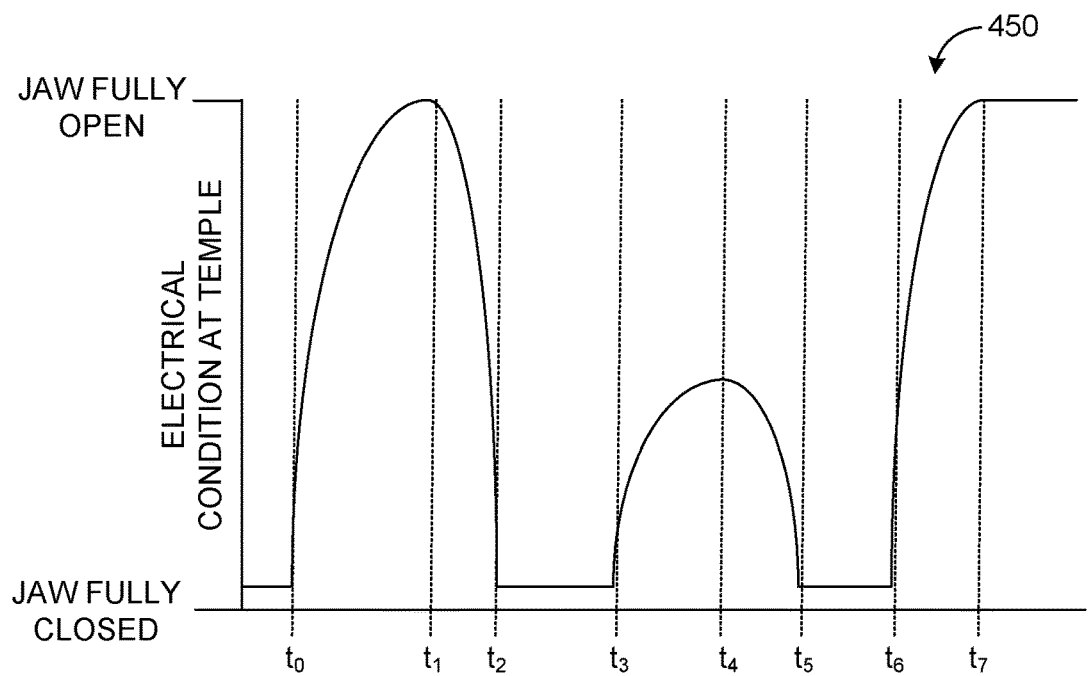
FIG. 4B shows an idealized graph indicating an electrical condition observed at a temple of a user based on jaw movement of the user.

As an example, FIG. 4B shows an idealized plot 450 showing an electrical condition detected by a temporal RF antenna as the jaw of a user moves from fully closed to fully open over time. At time t0, the user's jaw is fully closed, moving to fully open at time $t_1$. In concert, the electrical condition increases, decreasing to baseline as the user's jaw closes at time $t_2$. This sequence is repeated from time $t_3$ (closed) to time $t_4$ (open) to time $t_5$ (closed), though at time $t_4$, the user's jaw is only partially open, yielding a smaller magnitude of electrical condition. At time $t_6$, the user opens their jaw fully and holds their jaw open for a duration beginning at time $t_7$.

As shown, holding the jaw open or closed keeps the observed electrical condition in the same position, and thus the electrical activity need not be based solely on relative or active movement. In some examples, the temporal region 415 may not uniformly change based on jaw movement. As such, the HMD device may learn over time which portions are more informative, and thus activate antennas accordingly.

While movement is detected from baseline, some users will have an increased signal when open and low signal when closed, but others may generate the opposite polarity based on their head geometry. The amplitude of the electrical condition can provide an indication of the magnitude of opening—at least slightly, moderately, and fully open, and thus allow for the HMD device to distinguish between gum chewing, talking, singing opera, etc. The high SNR generated by the RF antenna allows for this discernment.

As such, electrical activity at the temporal region may be recorded and plotted against jawbone position for later comparison and inference of jawbone position. For example one or more machine learning models and/or classifiers may be trained with pairs of electrical activity and jawbone position. The training data sets may be derived from a plurality of users, and subsets used to classify activity for a particular user—for example, users with relatively similar facial characteristics who speak the same primary language. In some examples, models and/or classifiers may be generated for a particular user in a training and calibration phase of learning. In some examples, training data may be simulated based on sets of facial characteristics. Any of the training data examples may alternatively be stored in one or more lookup tables where they can be retrieved based on newly obtained data.

Figure 5A:
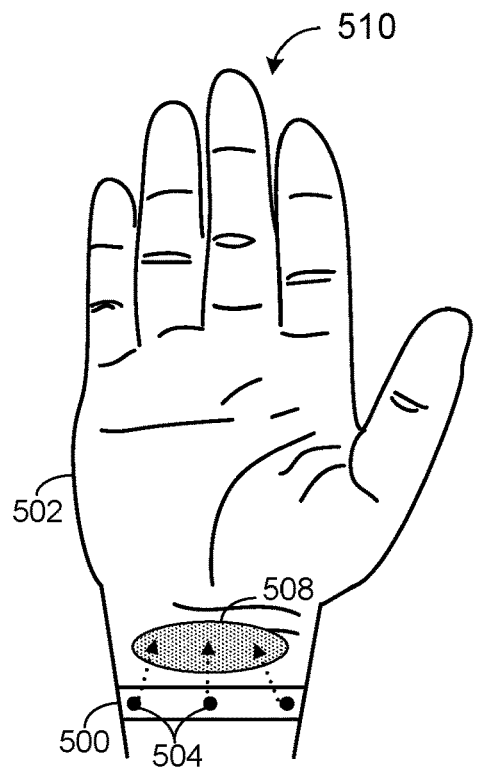
FIGS. 5A and 5B show an example of a wrist-worn computing device including an array of RF antennas.
Figure 5B:
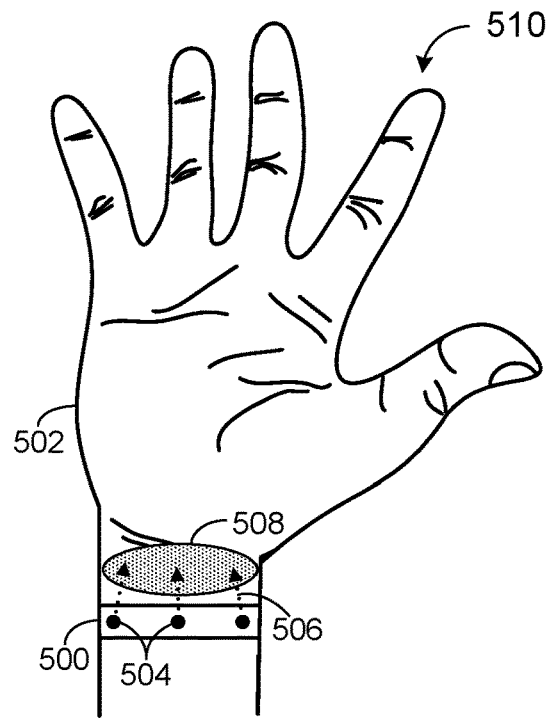

Though the present disclosure primarily focuses on computing devices worn on or near a user's face (e.g., as an HMD), it will be understood that this is not limiting. FIGS. 5A and 5B schematically illustrate another example computing device 500 that may implement any or all of the techniques described herein. Specifically, computing device 500 is a wrist-worn mobile device that is worn on the wrist of a human hand 502. Computing device 500 may, for example, take the form of a smartwatch, or other computing device having a wrist-wearable form factor.

As with HMD device 400, computing device 500 includes a plurality of RF antennas 504 configured to expose a human user body surface to an E-field 506. In this example, the wrist surface 508 of the human user is exposed to the E-field, at least part of which is positioned within a near-field region relative to the RF antennas when computing device 500 is being worn. As muscles and tendons of the wrist region couple the wrist to the fingers 510 of the user, movement of the fingers 510 may cause detectable movement of the wrist surface 508 which may be observed as a change in electrical condition at RF antennas 504.

As an example, the gesture formed by human hand 502 changes between FIG. 5A and FIG. 5B. Specifically, between FIGS. 5A and 5B, the hand forms a gesture in which the fingers and thumb are spread apart from one another. This is associated with muscular movements in the user's hand and wrist, which may cause a change in electrical conditions (e.g., a detectable change in voltage) at any or all of the plurality of RF antennas 504, as discussed above. Thus, by collecting data from each of the plurality of RF antennas, the computing device may classify the detected movement of the human hand. In some examples, one or more RF antennas 504 may be trained on specific portions of wrist surface 508 in order to discern movement of individual fingers or groups of fingers (e.g., above the ulnar collateral ligament to discern movement of the pinky and ring fingers of hand 502).

Figure 6:
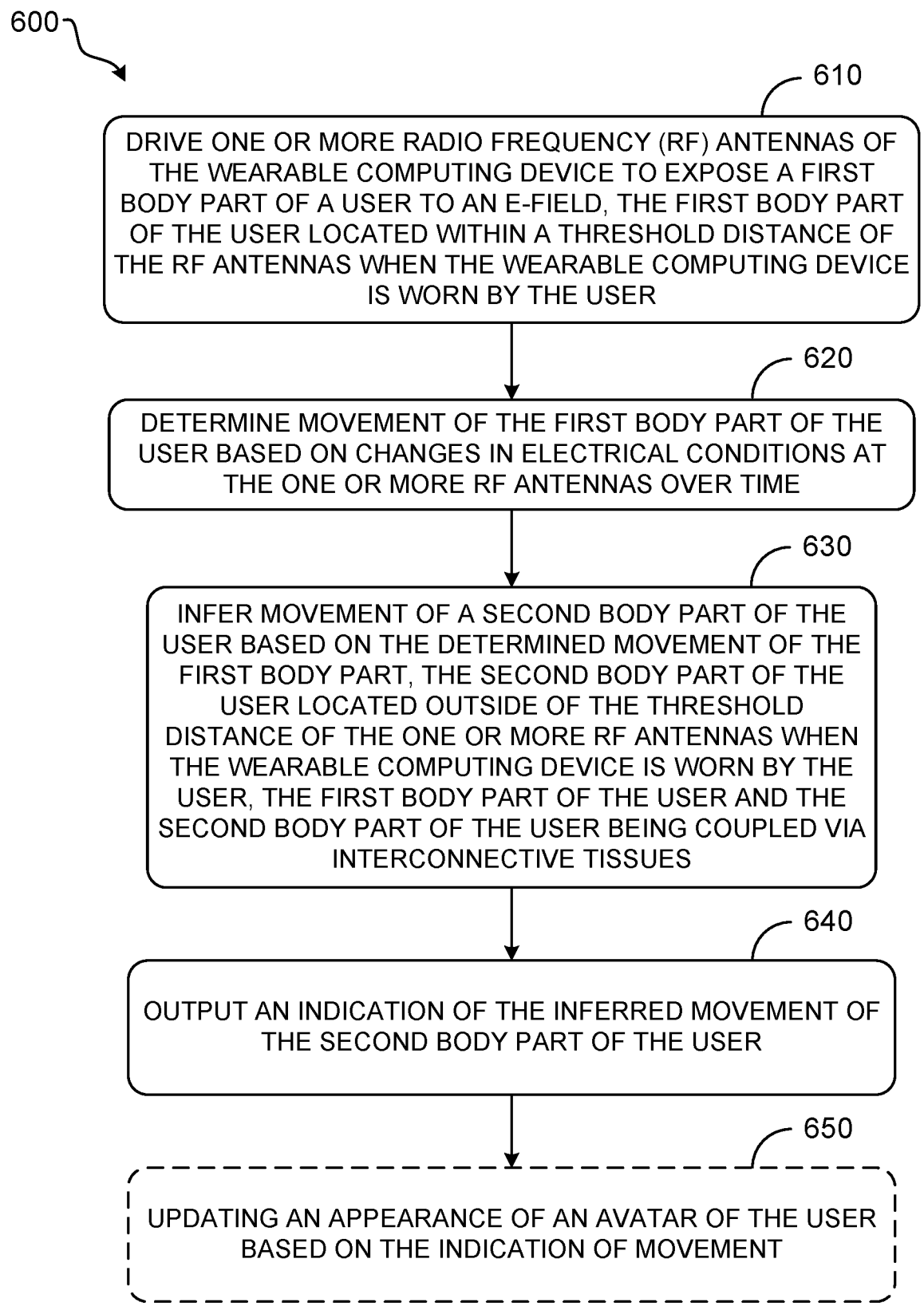
FIG. 6 is a flow diagram for an example method for operating a wearable computing device.

FIG. 6 shows a computer-implemented method 600 for operating a wearable computing device that includes an RF tracking system, such as HMD device 300 and RF face tracking system 302, or wrist-worn computing device 500 and RF antennas 504, according to an embodiment of the present disclosure. The wearable computing device may include other sensors outside of the RF face tracking system, such as microphones, cameras, IMUs, etc. as described with regard to HMD device 200. Method 600 may be performed at one or more processes of the wearable computing device, as an example. Additionally or alternatively, aspects of method 600 may be performed by one or more external computing devices communicatively coupled to the wearable computing device. The technical effect of implementing this method is an improvement in human-computer interaction.

At 610, method 600 includes driving a first channel of one or more RF antennas of the wearable computing device to expose a first body part of a user to an E-field, the first body part of the user located within a threshold distance of the RF antennas when the wearable computing device is worn by the user. As described, for a head-mounted display device, the first channel of RF antennas may be positioned on a temple piece of the HMD device, so that the first channel of RF antennas is positioned so as to be located within a threshold distance of a temporal region of a user when the head-mounted display device is worn. In an alternate embodiment, the wearable computing device may be a wrist-worn computing device, and the first channel of RF antennas may be positioned on or near a wrist region of the user when the wrist-worn computing device is worn.

At 620, method 600 includes determining movement of the first body part of the user based on changes in electrical conditions at the first channel of one or more RF antennas over time. For example, based on the changes in electrical conditions, the wearable computing device may determine whether the first body part of the user is moving towards or away from the RF antenna.

In some examples, method 600 may further include driving a second channel of one or more RF antennas to expose a third body part of the user to an E-field, the third body part of the user located within the threshold distance of the RF antennas when the wearable computing device is worn by the user, and may further include determining movement of the third body part of the user based on changes in electrical conditions at the second channel of one or more RF antennas over time. In other words, the wearable computing device may include multiple RF channels configured to monitor movement of multiple body parts of the user.

At 630, method 600 includes inferring movement of a second body part of the user based on the determined movement of the first body part, the second body part located outside of the threshold distance of the RF antenna when the wearable computing device is worn by the user, the first body part and the second body part coupled via interconnective tissues. Generically, interconnective tissues may include muscles, tendons, ligaments, skin, fascia, bones, etc. As described, when the first body part is a region of a wrist of the user, the second body part may be a finger of the user. In order to make a facial expression or hand gesture, the user necessarily has to move a muscle or tendon in the jaw or wrist. Such examples are not limiting—inferred movement of any two interconnected body parts can be performed with this methodology, provided the RF antennas can be brought into proximity to one or the other of the interconnected body parts.

One or more classifiers, machine learning models, neural networks, etc. may be trained to recognize a position of the second body part of the user based on electrical activity at the first body part of the user. Features may be extracted from the output of the RF face tracking system and fed to trained models or classifiers. Trained models or classifiers may be previously trained through supervised training based on labeled scenarios of the user's second body part in a plurality of conformations, such as jaw open, closed, partially open, etc. Some aspects and characteristics of these correlations may be stored in a cache or user/device history in order to inform future wear status discernment. Deterministic models may be trained to be highly accurate, thus removing the need for a neural network classifier, which may use additional power.

In some examples, additional features may be extracted from any additional sensors, such as microphones, IMUs, etc. and provided to the trained models or classifiers. For example, the IMUs may provide an indication of whether the HMD device is parallel to the ground, and thus indicate whether signals from RF antennas on one side of the device may be expected to be similar or different than signals from RF antennas on the other side of the device.

The model algorithms described herein may be trained and retrained via machine learning to determine how a particular user's temporal electrical activity changes with respect to jaw position. The trained model or classifier may receive classifiable features. Each sensor may employ one or more dedicated pre-processes or may collectively employ one or more pre-processes. Signal processing, such as smoothing, may be performed on the raw inputs from the RF antennas and IMUS, etc.

The correlations between extracted features and the body part conformations may be calculated and used to generate one or more confidence and/or likelihood scores. For example, decision boundaries between scenarios may be indicated, and a confidence generated based on a distance of the output of a machine learning model and a decision boundary. For example, a classification that is a threshold distance from a decision boundary will be assigned a high confidence, while a classification that is near a decision boundary will be assigned a lower confidence.

Returning to FIG. 6, at 640, method 600 includes outputting an indication of the inferred movement of the second body part. The indication of the inferred movement of the second body part may include a conformation, position, relative distance, deviation, etc. of the second body part, either static or in relation to a previous position. The indication may be provided to one or more other computing devices, may be recorded at the wearable computing device or any other communicatively coupled computing device, etc. In some examples, an indication may be provided to the user in the form of a visual or audio cue, for example.

In examples wherein the wearable computing device includes multiple channels of RF antennas, method 600 may further include inferring movement of a fourth body part of the user based on the determined movement of the third body part, the fourth body part located outside of the threshold distance of the RF antenna when the wearable computing device is worn by the user, the third body part and the fourth body part coupled via interconnective tissues. The wearable computing device may then output an indication of the inferred movement of the fourth body part.

In some examples, the fourth body part may moves in concert with the second body part. Movement of the second body part may thus be further inferred based on the determined movement of the third body part. For example, RF channels may be positioned on both temple pieces of an HMD. Movement of both a first temporal region and an opposite temporal of the users face may be used to determine movement of the user's jaw and mouth. In other examples, such as the wrist-worn computing device, the multiple channels may be used to determine movement of separate body parts, such as fingers.

At 650, method 600 optionally includes updating an appearance of an avatar of the user based on the indication of movement. Beyond just reporting "mouth open" or frown vs smile, or any discrete number of facial expressions, the jaw antenna data can be used to inform a photorealistic avatar. As shown in FIG. 1, a user engaged with a wearable computing device may be using the wearable computing device to control the appearance of an avatar that may be perceived by one or more other users in a virtual or augmented reality environment, for example. The detected movement, of a jawbone of the user, for example, may be translated into movement (or non-movement) of the mouth of the avatar.

As an example, the wearable computing device may include one or more microphones, and the wearable computing device may configured to arbitrate whether sounds captured by the one or more microphones are attributable to the user based on the indication of the inferred movement of the jawbone of the user. For example, background noise that may otherwise be mistaken for speech of the user may be ignored, and the avatar not updated based on that background noise. Alternatively, facial expressions that do not result in audible noise may indeed be used to update the avatar's appearance. This may allow for the relaxing of requirements on audio beam forming in the wearable computing device.

Generating and rendering avatars are far from the only use for method 600. For example, users wearing head-mounted displays may employ jaw tracking for applications such as learning a foreign language, singing training, acting, etc. Wrist-worn computing devices may lend themselves as part of typing or piano training, physical activities (e.g., throwing a baseball, swinging a golf club), physical therapy, and other applications wherein monitoring the movements of the hands are informative. For both head and wrist applications, RF tracking may be used to allow users to have increased natural language inputs for operating a computing device. Other wearable technology may also benefit from implementing this methodology, allowing monitoring and recording of body movements with sensors that are conveniently, and socially acceptably placed on the body.

In some embodiments, the methods and processes described herein may be tied to a computing system of one or more computing devices. In particular, such methods and processes may be implemented as a computer-application program or service, an application-programming interface (API), a library, and/or other computer-program product.

Figure 7:
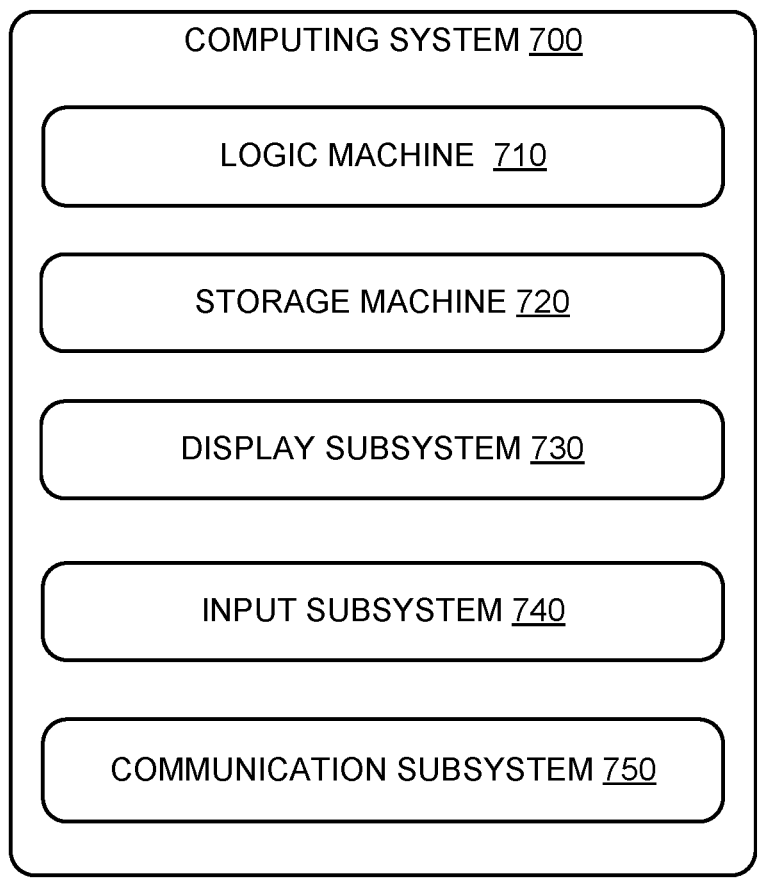
FIG. 7 schematically shows an example computing device.

FIG. 7 schematically shows a non-limiting embodiment of a computing system 700 that can enact one or more of the methods and processes described above. Computing system 700 is shown in simplified form. Computing system 700 may take the form of one or more personal computers, server computers, tablet computers, home-entertainment computers, network computing devices, gaming devices, mobile computing devices, mobile communication devices (e.g., smart phone), and/or other computing devices.

Computing system 700 includes a logic machine 710 and a storage machine 720. Computing system 700 may optionally include a display subsystem 730, input subsystem 740, communication subsystem 750, and/or other components not shown in FIG. 7. For example, head-mounted display devices 110, 200, 300, 405, and 500 may be examples of computing system 700. Controllers 230 and 301 may be examples of logic machine 710. Displays 210, 212, 310, and 312 may be examples of display subsystem 730. Cameras 232 and 234, eye-tracking system 220, and face tracking systems 240 and 302 may be examples of input subsystem 740.

Logic machine 710 includes one or more physical devices configured to execute instructions. For example, the logic machine may be configured to execute instructions that are part of one or more applications, services, programs, routines, libraries, objects, components, data structures, or other logical constructs. Such instructions may be implemented to perform a task, implement a data type, transform the state of one or more components, achieve a technical effect, or otherwise arrive at a desired result.

The logic machine may include one or more processors configured to execute software instructions. Additionally or alternatively, the logic machine may include one or more hardware or firmware logic machines configured to execute hardware or firmware instructions. Processors of the logic machine may be single-core or multi-core, and the instructions executed thereon may be configured for sequential, parallel, and/or distributed processing. Individual components of the logic machine optionally may be distributed among two or more separate devices, which may be remotely located and/or configured for coordinated processing. Aspects of the logic machine may be virtualized and executed by remotely accessible, networked computing devices configured in a cloud-computing configuration.

Storage machine 720 includes one or more physical devices configured to hold instructions executable by the logic machine to implement the methods and processes described herein. When such methods and processes are implemented, the state of storage machine 720 may be transformed—e.g., to hold different data.

Storage machine 720 may include removable and/or built-in devices. Storage machine 720 may include optical memory (e.g., CD, DVD, HD-DVD, Blu-Ray Disc, etc.), semiconductor memory (e.g., RAM, EPROM, EEPROM, etc.), and/or magnetic memory (e.g., hard-disk drive, floppy-disk drive, tape drive, MRAM, etc.), among others. Storage machine 720 may include volatile, nonvolatile, dynamic, static, read/write, read-only, random-access, sequential-access, location-addressable, file-addressable, and/or content-addressable devices.

It will be appreciated that storage machine 720 includes one or more physical devices. However, aspects of the instructions described herein alternatively may be propagated by a communication medium (e.g., an electromagnetic signal, an optical signal, etc.) that is not held by a physical device for a finite duration.

Aspects of logic machine 710 and storage machine 720 may be integrated together into one or more hardware-logic components. Such hardware-logic components may include field-programmable gate arrays (FPGAs), program- and application-specific integrated circuits (PASIC/ASICs), program- and application-specific standard products (PSSP/ASSPs), system-on-a-chip (SOC), and complex programmable logic devices (CPLDs), for example.

The terms "module," "program," and "engine" may be used to describe an aspect of computing system 700 implemented to perform a particular function. In some cases, a module, program, or engine may be instantiated via logic machine 710 executing instructions held by storage machine 720. It will be understood that different modules, programs, and/or engines may be instantiated from the same application, service, code block, object, library, routine, API, function, etc. Likewise, the same module, program, and/or engine may be instantiated by different applications, services, code blocks, objects, routines, APIs, functions, etc. The terms "module," "program," and "engine" may encompass individual or groups of executable files, data files, libraries, drivers, scripts, database records, etc.

It will be appreciated that a "service," as used herein, is an application program executable across multiple user sessions. A service may be available to one or more system components, programs, and/or other services. In some implementations, a service may run on one or more server-computing devices.

Machine learning models as referenced above may be implemented using any suitable combination of state-of-the-art and/or future machine learning and/or other artificial intelligence techniques. Non-limiting examples of techniques that may be incorporated in an implementation of one or more machines include support vector machines, multilayer neural networks, convolutional neural networks (e.g., including spatial convolutional networks for processing images and/or videos, temporal convolutional neural networks, and/or any other suitable convolutional neural networks configured to convolve and pool features across one or more temporal and/or spatial dimensions), recurrent neural networks (e.g., long short-term memory networks), associative memories (e.g., lookup tables, hash tables, Bloom Filters, Neural Turing Machine and/or Neural Random Access Memory), unsupervised spatial and/or clustering methods (e.g., nearest neighbor algorithms, topological data analysis, and/or k-means clustering), and/or graphical models (e.g., (hidden) Markov models, Markov random fields, (hidden) conditional random fields, and/or AI knowledge bases).

In some examples, the methods and processes described herein may be implemented using one or more differentiable functions, wherein a gradient of the differentiable functions may be calculated and/or estimated with regard to inputs and/or outputs of the differentiable functions (e.g., with regard to training data, and/or with regard to an objective function). Such methods and processes may be at least partially determined by a set of trainable parameters. Accordingly, the trainable parameters for a particular method or process may be adjusted through any suitable training procedure, in order to continually improve functioning of the method or process.

Non-limiting examples of training procedures for adjusting trainable parameters include supervised training (e.g., using gradient descent or any other suitable optimization method), zero-shot, few-shot, unsupervised learning methods (e.g., classification based on classes derived from unsupervised clustering methods), reinforcement learning (e.g., deep Q learning based on feedback) and/or generative adversarial neural network training methods, belief propagation, RANSAC (random sample consensus), contextual bandit methods, maximum likelihood methods, and/or expectation maximization. In some examples, a plurality of methods, processes, and/or components of systems described herein may be trained simultaneously with regard to an objective function measuring performance of collective functioning of the plurality of components (e.g., with regard to reinforcement feedback and/or with regard to labelled training data). Simultaneously training the plurality of methods, processes, and/or components may improve such collective functioning. In some examples, one or more methods, processes, and/or components may be trained independently of other components (e.g., offline training on historical data).

When included, display subsystem 730 may be used to present a visual representation of data held by storage machine 720. This visual representation may take the form of a graphical user interface (GUI). As the herein described methods and processes change the data held by the storage machine, and thus transform the state of the storage machine, the state of display subsystem 730 may likewise be transformed to visually represent changes in the underlying data. Display subsystem 730 may include one or more display devices utilizing virtually any type of technology. Such display devices may be combined with logic machine 710 and/or storage machine 720 in a shared enclosure, or such display devices may be peripheral display devices.

When included, input subsystem 740 may comprise or interface with one or more user-input devices such as a keyboard, mouse, touch screen, or game controller. In some embodiments, the input subsystem may comprise or interface with selected natural user input (NUI) componentry. Such componentry may be integrated or peripheral, and the transduction and/or processing of input actions may be handled on- or off-board. Example NUI componentry may include a microphone for speech and/or voice recognition; an infrared, color, stereoscopic, and/or depth camera for machine vision and/or gesture recognition; a head tracker, eye tracker, accelerometer, and/or gyroscope for motion detection and/or intent recognition; as well as electric-field sensing componentry for assessing brain activity.

When included, communication subsystem 750 may be configured to communicatively couple computing system 700 with one or more other computing devices. Communication subsystem 750 may include wired and/or wireless communication devices compatible with one or more different communication protocols. As non-limiting examples, the communication subsystem may be configured for communication via a wireless telephone network, or a wired or wireless local- or wide-area network. In some embodiments, the communication subsystem may allow computing system 700 to send and/or receive messages to and/or from other devices via a network such as the Internet.

In one example, a method for a wearable computing device, comprises driving a first channel of one or more radio frequency (RF) antennas of the wearable computing device to expose a first body part of a user to a first E-field, the first body part of the user located within a threshold distance of the first channel of one or more RF antennas when the wearable computing device is worn by the user; determining movement of the first body part of the user based on changes in electrical conditions at the first channel of one or more RF antennas over time; inferring movement of a second body part of the user based on the determined movement of the first body part, the second body part of the user located outside of the threshold distance of the first channel of one or more RF antennas when the wearable computing device is worn by the user, the first body part of the user and the second body part of the user being coupled via interconnective tissues; and outputting an indication of the inferred movement of the second body part of the user. In such an example, or any other example, the method additionally or alternatively comprises driving a second channel of one or more RF antennae to expose a third body part of the user to a second E-field, the third body part of the user located at within the threshold distance of the second channel of one or more RF antennas when the wearable computing device is worn by the user; and determining movement of the third body part of the user based on changes in electrical conditions at the second channel of one or more RF antennas over time. In any of the preceding examples, or any other example, the method additionally or alternatively comprises inferring movement of a fourth body part of the user based on the determined movement of the third body part, the fourth body part located outside of the threshold distance of the second channel of one or more RF antennas when the wearable computing device is worn by the user, the third body part and the fourth body part coupled via interconnective tissues; and outputting an indication of the inferred movement of the fourth body part. In any of the preceding examples, or any other example, the fourth body part additionally or alternatively moves in concert with the second body part, and wherein the movement of the second body part is further inferred based on the determined movement of the third body part. In any of the preceding examples, or any other example, outputting the indication of movement of the second body part additionally or alternatively includes updating an appearance of an avatar of the user based on the indication of movement. In any of the preceding examples, or any other example, the first body part is additionally or alternatively a region of a wrist of the user, and the second body part is additionally or alternatively finger of the user. In any of the preceding examples, or any other example, the first body part is additionally or alternatively a temporal region of the user's face, and the second body part is additionally or alternatively a jawbone of the user. The technical effect of implementing this method is an improvement in human-computer interaction.

In another example, a head-mounted display device, comprises a frame; left and right temple pieces extending from the frame; a radio frequency (RF) face tracking system, comprising one or more temple RF channels positioned on one or both of the left and right temple pieces so as to be located within a threshold distance of one or more temporal regions of a user when the head-mounted display device is worn, each temple RF channel including one or more antennas; and a controller configured to: drive a first channel of temple RF antennas to expose a first temporal region of the one or more temporal regions to an E-field; determine movement of the first temporal region based on changes in electrical conditions at the first channel of temple RF antennas over time; infer movement of a jawbone of the user based on the determined movement of the first temporal region; and output an indication of the inferred movement of the jawbone of the user. In such an example, or any other example, the first channel of temple RF antennas is additionally or alternatively positioned at a threshold distance from a point of contact between a respective temple piece and an ear of the user when the head-mounted display device is worn by the user. In any of the preceding examples, or any other example, the first channel of temple RF antennas is additionally or alternatively positioned on a body-facing surface of a respective temple piece. In any of the preceding examples, or any other example, the head-mounted display device additionally or alternatively comprises a second channel of temple RF antennas positioned on an opposite temple piece from the first channel of temple RF antennas, and the controller is additionally or alternatively configured to: drive the second channel of temple RF antennas to expose a second temporal region of the user to an E-field, the second temporal region being opposite the first temporal region; determine movement of the second temporal region based on changes in electrical conditions at the second channel of temple RF antennas over time; infer movement of the jawbone of the user based on the determined movement of the temporal region and the opposite temporal region. In any of the preceding examples, or any other example, the indication of inferred movement of the jawbone of the user additionally or alternatively includes a current jaw conformation of the user. In any of the preceding examples, or any other example, the controller is additionally or alternatively configured to update an appearance of an avatar of the user based on the indication of movement. In any of the preceding examples, or any other example, the head-mounted display device additionally or alternatively comprises one or more microphones, and wherein the controller is further configured to arbitrate whether sounds captured by the one or more microphones are attributable to the user based on the indication of the inferred movement of the jawbone of the user. The technical effect of implementing this device is an improvement in human-computer interaction.

In yet another example, a method for a head-mounted display device comprises driving a first channel of one or more RF antennas positioned on a temple piece of the head-mounted display device to expose a temporal region of the user to an E-field; determining movement of the temporal region based on changes in electrical conditions at the first channel of one or more RF antennas over time; inferring movement of a jawbone of the user based on the determined movement of the temporal region; and outputting an indication of the inferred movement of the jawbone of the user. In such an example, or any other example, the first channel of one or more RF antennas are additionally or alternatively positioned at a threshold distance from a point of contact between the temple piece and an ear of the user when the head-mounted display device is worn by the user. In any of the preceding examples, or any other example, the first channel of temple RF antennas are additionally or alternatively positioned on a body-facing surface of the temple piece. In any of the preceding examples, or any other example, the indication of inferred movement of the jawbone of the user additionally or alternatively includes a current jaw conformation of the user. In any of the preceding examples, or any other example, the method additionally or alternatively comprises updating an appearance of an avatar of the user based on the indication of movement. In any of the preceding examples, or any other example, the method additionally or alternatively comprises capturing sounds via one or more microphones of the head-mounted display device; and arbitrating whether the sounds captured by the one or more microphones are attributable to the user based on the indication of the inferred movement of the jawbone of the user. The technical effect of implementing this method is an improvement in human-computer interaction.

It will be understood that the configurations and/or approaches described herein are exemplary in nature, and that these specific embodiments or examples are not to be considered in a limiting sense, because numerous variations are possible. The specific routines or methods described herein may represent one or more of any number of processing strategies. As such, various acts illustrated and/or described may be performed in the sequence illustrated and/or described, in other sequences, in parallel, or omitted. Likewise, the order of the above-described processes may be changed.

The subject matter of the present disclosure includes all novel and non-obvious combinations and sub-combinations of the various processes, systems and configurations, and other features, functions, acts, and/or properties disclosed herein, as well as any and all equivalents thereof.

The invention claimed is:

1. A method for a wearable computing device, comprising:
    driving a first channel of one or more radio frequency (RF) antennas of the wearable computing device to expose a first body part of a user to a first E-field, the first body part of the user located within a threshold distance of the first channel of one or more RF antennas when the wearable computing device is worn by the user;
    determining movement of the first body part of the user based on changes in electrical conditions at the first channel of one or more RF antennas over time;
    inferring movement of a second body part of the user based on the determined movement of the first body part, the second body part of the user located outside of the threshold distance of the first channel of one or more RF antennas when the wearable computing device is worn by the user, the first body part of the user and the second body part of the user being coupled via interconnective tissues; and
    outputting an indication of the inferred movement of the second body part of the user.

2. The method of claim 1, further comprising:
driving a second channel of one or more RF antennae to expose a third body part of the user to a second E-field, the third body part of the user located at within the threshold distance of the second channel of one or more RF antennas when the wearable computing device is worn by the user; and
determining movement of the third body part of the user based on changes in electrical conditions at the second channel of one or more RF antennas over time.

3. The method of claim 2, further comprising:
inferring movement of a fourth body part of the user based on the determined movement of the third body part, the fourth body part located outside of the threshold distance of the second channel of one or more RF antennas when the wearable computing device is worn by the user, the third body part and the fourth body part coupled via interconnective tissues; and
outputting an indication of the inferred movement of the fourth body part.

4. The method of claim 3, wherein the fourth body part moves in concert with the second body part, and wherein the movement of the second body part is further inferred based on the determined movement of the third body part.

5. The method of claim 1, wherein outputting the indication of movement of the second body part includes updating an appearance of an avatar of the user based on the indication of movement.

6. The method of claim 1, wherein the first body part is a region of a wrist of the user, and the second body part is a finger of the user.

7. The method of claim 1, wherein the first body part is a temporal region of the user's face, and the second body part is a jawbone of the user.

8. A head-mounted display device, comprising:
a frame;
left and right temple pieces extending from the frame;
a radio frequency (RF) face tracking system, comprising one or more temple RF channels positioned on one or both of the left and right temple pieces so as to be located within a threshold distance of one or more temporal regions of a user when the head-mounted display device is worn, each temple RF channel including one or more antennas; and
a controller configured to:
drive a first channel of temple RF antennas to expose a first temporal region of the one or more temporal regions to an E-field;
determine movement of the first temporal region based on changes in electrical conditions at the first channel of temple RF antennas over time;
infer movement of a jawbone of the user based on the determined movement of the first temporal region; and
output an indication of the inferred movement of the jawbone of the user.

9. The head-mounted display device of claim 8, wherein the first channel of temple RF antennas is positioned at a threshold distance from a point of contact between a respective temple piece and an ear of the user when the head-mounted display device is worn by the user.

10. The head-mounted display device of claim 8, wherein the first channel of temple RF antennas is positioned on a body-facing surface of a respective temple piece.

11. The head-mounted display device of claim 8, further comprising a second channel of temple RF antennas positioned on an opposite temple piece from the first channel of temple RF antennas, and wherein the controller is further configured to:
drive the second channel of temple RF antennas to expose a second temporal region of the user to an E-field, the second temporal region being opposite the first temporal region;
determine movement of the second temporal region based on changes in electrical conditions at the second channel of temple RF antennas over time;
infer movement of the jawbone of the user based on the determined movement of the temporal region and the opposite temporal region.

12. The head-mounted display device of claim 8, wherein the indication of inferred movement of the jawbone of the user includes a current jaw conformation of the user.

13. The head-mounted display device of claim 8, wherein the controller is further configured to:
update an appearance of an avatar of the user based on the indication of movement.

14. The head-mounted display device of claim 13, further comprising one or more microphones, and wherein the controller is further configured to:
arbitrate whether sounds captured by the one or more microphones are attributable to the user based on the indication of the inferred movement of the jawbone of the user.

15. A method for a head-mounted display device, comprising:
driving a first channel of one or more RF antennas positioned on a temple piece of the head-mounted display device to expose a temporal region of the user to an E-field;
determining movement of the temporal region based on changes in electrical conditions at the first channel of one or more RF antennas over time;
inferring movement of a jawbone of the user based on the determined movement of the temporal region; and
outputting an indication of the inferred movement of the jawbone of the user.

16. The method of claim 15, wherein the first channel of one or more RF antennas are positioned at a threshold distance from a point of contact between the temple piece and an ear of the user when the head-mounted display device is worn by the user.

17. The method of claim 15, wherein the first channel of temple RF antennas are positioned on a body-facing surface of the temple piece.

18. The method of claim 15, wherein the indication of inferred movement of the jawbone of the user includes a current jaw conformation of the user.

19. The method of claim 15, further comprising:
updating an appearance of an avatar of the user based on the indication of movement.

20. The method of claim 18, further comprising:
capturing sounds via one or more microphones of the head-mounted display device; and
arbitrating whether the sounds captured by the one or more microphones are attributable to the user based on the indication of the inferred movement of the jawbone of the user.

* * * * *